United States Patent
Petersen et al.

Patent Number: 5,571,812
Date of Patent: Nov. 5, 1996

[54] 7-AMINO-1-CYCLOPROPYL-6,8-DIHALOGENO-1,4-DIHYDRO-4-OXO-3-QUINOLINECARBOXYLIC ACID ANTIBACTERIAL AGENTS

[75] Inventors: Uwe Petersen, Leverkusen; Klaus Grohe, Odenthal; Hans-Joachim Zeiler, Velbert; Karl G. Metzger, Wuppertal, all of Germany

[73] Assignee: Bayer Aktiengesellschaft, Leverkusen, Germany

[21] Appl. No.: 875,572

[22] Filed: Apr. 27, 1992

Related U.S. Application Data

[63] Continuation of Ser. No. 735,500, May 17, 1985, abandoned.

Foreign Application Priority Data

Jun. 4, 1984 [DE] Germany ............... 34 20 743.0

[51] Int. Cl.⁶ ............... A61K 31/495; A61K 31/47; C07D 401/04
[52] U.S. Cl. ............... 514/254; 514/312; 544/363; 546/156
[58] Field of Search ............... 544/363; 546/156; 514/254.30, 312

[56] References Cited

U.S. PATENT DOCUMENTS

| | | | |
|---|---|---|---|
| 4,359,578 | 11/1982 | Matsumoto et al. | 544/363 |
| 4,398,029 | 8/1983 | Irikura et al. | 544/363 |
| 4,544,658 | 10/1985 | Petersen et al. | 544/363 |
| 4,556,658 | 12/1985 | Grohe et al. | 544/363 |
| 4,563,459 | 1/1986 | Grohe et al. | 544/363 |
| 4,599,334 | 7/1986 | Petersen et al. | 544/363 |
| 4,771,054 | 8/1986 | Domagala et al. | 514/312 |

FOREIGN PATENT DOCUMENTS

| | | |
|---|---|---|
| 899399 | 4/1984 | Belgium . |
| 0049355 | 4/1982 | European Pat. Off. . |
| 0126355 | 11/1984 | European Pat. Off. . |
| 3420743 | 6/1984 | Germany . |
| 60-222448 | 11/1985 | Japan ............... 544/363 |
| 2057440 | 4/1981 | United Kingdom . |

OTHER PUBLICATIONS

Wise, et al., "Antimicrobal Agents And Chemotherapy", 1983, vol. 23(4) pp. 559–564.

*Primary Examiner*—Bernard Dentz
*Attorney, Agent, or Firm*—Sprung Horn Kramer & Woods

[57] ABSTRACT

The invention is related to 7-amino-1-cyclopropyl-6,8-dihalogeno-1,4-dihydro-4-oxo-3-quinoline-carboxylic acids of the formula (I)

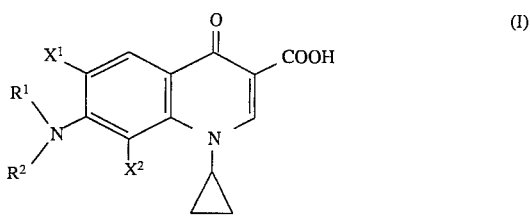

in which $X^1$, $X^2$, $R^1$ and $R^2$ have the meaning as pointed out in the following specification. Moreover, the invention is related to a process for the production of the compounds of formula (I) and to antibacterial agents containing them.

8 Claims, No Drawings

7-AMINO-1-CYCLOPROPYL-6,8-DIHALOGENO-1,4-DIHYDRO-4-OXO-3-QUINOLINECARBOXYLIC ACID ANTIBACTERIAL AGENTS

This application is a continuation of application Ser. No. 06/735,500, filed May 17, 1985, now abandoned.

The present invention relates to new 7-amino-1-cyclopropyl-6,8-dihalogeno-1,4-dihydro-4-oxo-3-quinolinecarboxylic acids, process for their preparation and anti-bacterial agents containing them.

The new 7-amino-1-cyclopropyl-6,8-dihalogeno-1,4-dihydro- 4-oxo-3-quinolinecarboxylic acids of the formula (I) have been found,

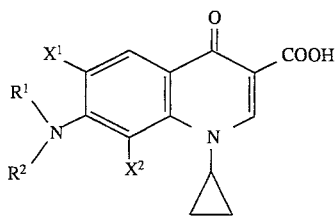 (I)

in which $X^1$ and $X^2$ which can be identical or different, represent chlorine or fluorine, but cannot both be fluorine, and $R^1$ and $R^2$ together with the nitrogen atom to which they are bonded, form a 5- or 6-membered heterocyclic ring which can contain in addition, as ring member, the atoms or groups —O—, —S—, —SO—, —SO$_2$—, >N—$R^3$ or

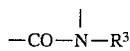

and which can optionally be substituted on the carbon atoms once to three times by $C_{1-4}$-alkyl, phenyl or cyclohexyl, each of which is optionally substituted once to three times by chlorine, fluorine, bromine, methyl, phenyl, hydroxyl, methoxy, benzyloxy, nitro or piperidino, 2-thienyl, hydroxyl, alkoxy having 1 to 3 carbon atoms, amino, methylamino or ethyl amino, $R^3$ representing hydrogen, a branched or unbranched alkyl, alkenyl or alkinyl group having 1 to 6 carbon atoms which can optionally be substituted by one or two hydroxyl, alkoxy, alkylamino or dialkylamino groups having 1 to 3 carbon atoms for an alkyl radical, the cyano group, or the alkoxycarbonyl group having 1 to 4 carbon atoms in the alcohol moiety, a phenylalkyl group which is optionally substituted in the phenyl radical and has up to 4 carbon atoms in the aliphatic moiety, a phenacyl radical which is optionally substituted once or twice by hydroxyl, methoxy, chlorine or fluorine, or an oxoalkyl radical having up to 6 carbon atoms, furthermore denoting a radical COR$^4$, CN or SO$_2$R$^5$, $R^4$ representing hydrogen, straight-chain or branched alkyl which has 1 to 4 carbon atoms and is optionally substituted by 1 or 2 substituents from the group comprising amino, alkoxycarbonyl having 1 to 3 carbon atoms in the alkyl moiety, carboxyl or alkoxy having 1 to 3 carbon atoms, or halogen such as chlorine, bromine or fluorine, or representing alkoxy having 1 to 4 carbon atoms, amino, alkylamino or dialkylamino having 1 to 5 carbon atoms in the alkyl moiety, and $R^5$ representing straight-chain or branched alkyl having 1 to 3 carbon atoms, and their pharmaceutically utilizable hydrates, acid addition salts, alkali metal, alkaline earth metal and guanidinium salts, which have high antibacterial activity.

Thus they are suitable as active compounds for human and veterinary medicine, veterinary medicine also including treatment of fish for the therapy or prevention of bacterial infections.

Preferred compounds of the formula (I) are those in which $X^1$ and $X^2$, which can be identical or different, represent chlorine or fluorine, but cannot both be fluorine, and $R^1$ and $R^2$ together with the nitrogen atom to which they are bonded, can form a 5- or 6- membered heterocyclic ring which can contain in addition, as ring member, the atoms or groups —O—, —S—, —SO$_2$—, N—$R^3$ or

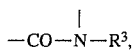

and which can optionally be substituted on the carbon atoms once to twice by $C_1$-$C_3$-alkyl, cyclohexyl, phenyl which is optionally substituted once or twice by chlorine, fluorine, bromine, methyl, phenyl, hydroxyl, meth oxy, benzyloxy, nitro or piperidino, 2-thienyl, hydroxyl, amino or methylamino, $R^3$ representing hydrogen, a branched or unbranched alkyl, alkenyl or alkinyl group having 1 to 4 carbon atoms, which can optionally be substituted by one or two hydroxyl groups, or a phenacyl radical, an oxoalkyl radical having up to 5 carbon atoms, or representing a radical COR$^4$, $R^4$ denoting hydrogen, straight-chain or branched alkyl having 1 to 3 carbon atoms, alkoxy having 1 to 3 carbon atoms, amino, alkylamino or dialkyl-amino having 1 to 3 carbon atoms in the alkyl moiety.

Particularly preferred compounds of the formula (I) are those in which $X^1$ and $X^2$ which can be identical or different, represent chlorine or fluorine, but cannot both be fluorine, and $R^1$ and $R^2$ together with the nitrogen atom to which they are bonded, can form a 5- or 6-membered heterocyclic ring which can contain in addition, as ring member, an oxygen atom or the groups N—$R^3$ or

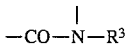

and which can optionally be substituted on the carbon atoms once or twice by $C_1$-$C_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, $R^3$ representing hydrogen, a branched or unbranched alkyl group having 1 to 3 carbon atoms which can optionally be substituted by one or two hydroxyl groups, or a phenacyl radical, an oxoalkyl radical having up to 4 carbon atoms or a radical COR$^4$, $R^4$ denoting hydrogen or alkyl having one or two carbon atoms.

It has also been found that the compounds of the formula (I) are obtained when the 1-cyclopropyl-7-halogeno-1,4-dihydro-4-oxo-3-quinolinecarboxylic acids of the formula (II)

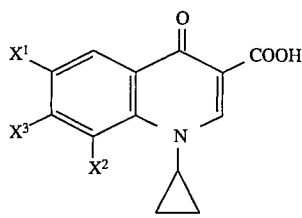

in which

X¹ and X² have the abovementioned meaning, and

X³ represents halogen, preferably chlorine or fluorine, are reacted with amines of the formula (III)

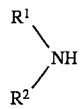

in which

R¹ and R² have the abovementioned meaning, where appropriate in the presence of acid-binding agents (method A).

Compounds according to the invention, of the formula (I), can also be obtained by reacting a 7-(1-piperazinyl)-3-quinolonecarboxylic acid of the formula (IV)

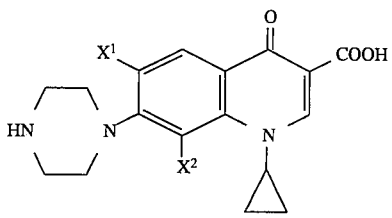

in which

X¹ and X² have the abovementioned meaning, and the piperazinyl radical can be substituted on the carbon atoms 1–3 times by $C_1$–$C_4$-alkyl, 2-thienyl or optionally substituted cyclohexyl or phenyl, with compounds of the formula (V)

in which

R³ has the abovementioned meaning but cannot be hydrogen, and

X denotes fluorine, chlorine, bromine, iodine, hydroxyl, acyloxy, ethoxy, phenoxy or 4-nitrophenoxy, where appropriate in the presence of acid-binding agents (method B).

Compounds according to the invention, of the formula (I), are also obtained when 7-(1-piperazinyl)-3-quinolonecarboxylic acid of the formula (IV), in which the piperazinyl radical can be substituted on the carbon atoms 1–3 times by $C_1$–$C_4$-alkyl,2-thienyl or optionally substituted cyclohexyl or phenyl, is reacted with Michael acceptors of the formula (VI)

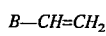

in which

B represents CN, CO-R⁶ or COOR⁷,

R⁶ representing methyl or ethyl, and

R⁷ representing methyl, ethyl, n- or i-propyl, (method C).

When, in the reaction by method A, 2-methylpiperazine and 6-chloro-1-cyclopropyl-7,8-difluoro-1,4-dihydro-4-oxo-3-quinolinecarboxylic acid are used as starting materials, then the course of the reaction can be represented by the equation below:

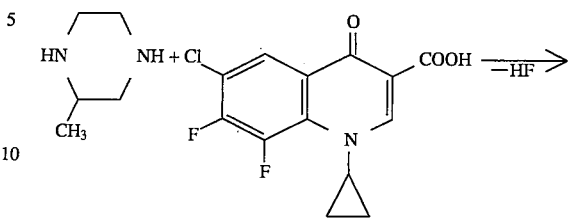

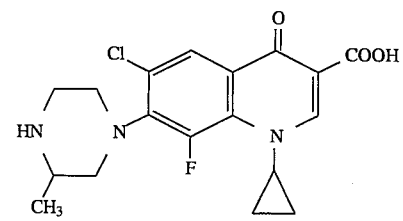

When, in the reaction by method B, ethyl iodide and 6-chloro-1-cyclopropyl-8-fluoro-1,4-dihydro-4-oxo-7-(1-piperazinyl)-3-quinolinecarboxylic acid are used as starting materials, then the course of the reaction can be represented by the equation below:

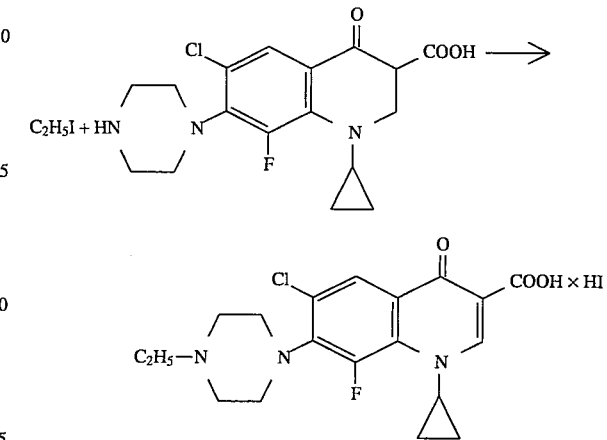

When, for example in the reaction of (IV) with (V) by method B, 6-chloro-1-cyclopropyl-8-fluoro-1,4-dihydro-7-(3-methyl-1-piperazinyl)-4-oxo-3-quinolinecarboxylic acid and formic acetic anhydride are used as starting compounds, then the course of the reaction can be represented by the equation below:

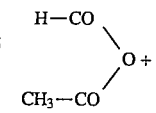

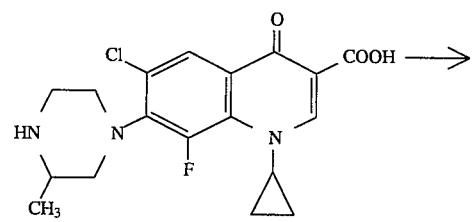

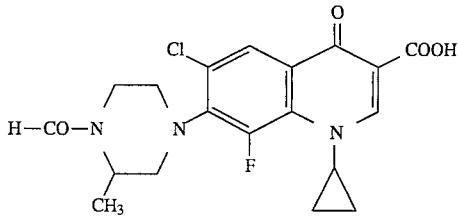

When, for example by method C, 6-chloro-1-cyclopropyl-8-fluoro-1,4-dihydro-4-oxo-7-(1-piperazinyl)-3-quinolinecarboxylic acid and methyl vinyl ketone are used as starting compounds, then the course of the reaction can be represented by the equation below:

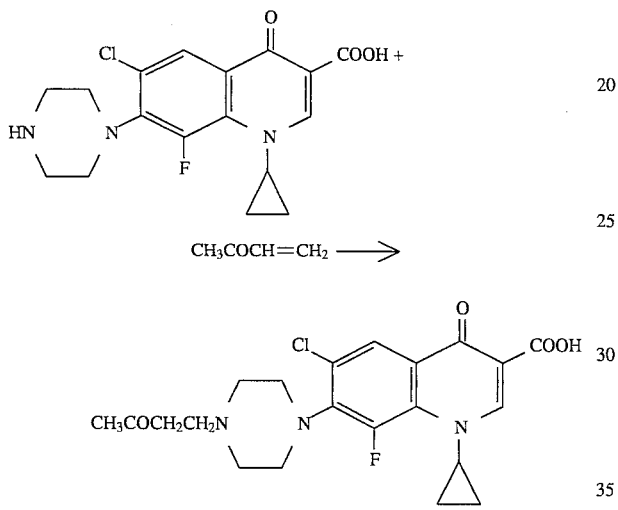

The 1-cyclopropyl-6,7,8-trihalogeno-1,4-dihydro-4-oxo-3-quinolinecarboxylic acids of the formula (II) which can be used as starting materials by method A can be prepared in accordance with the following reaction scheme:

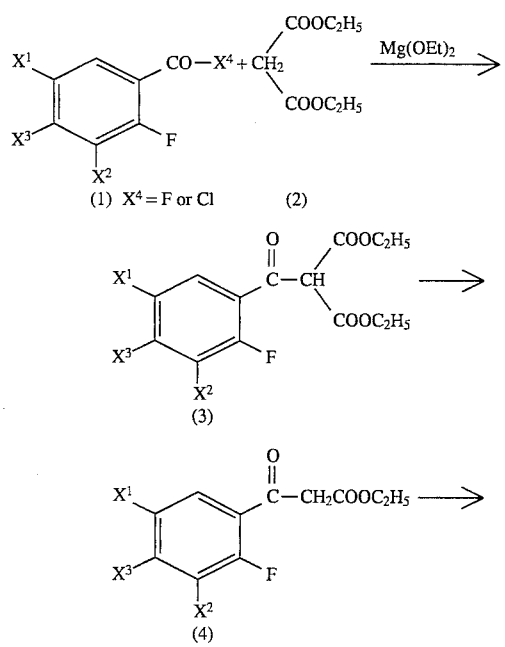

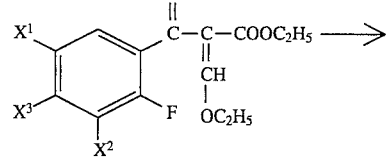

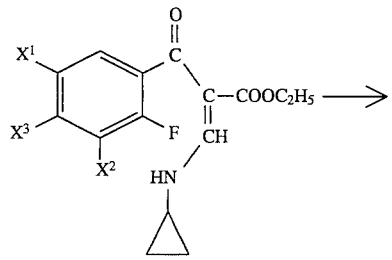

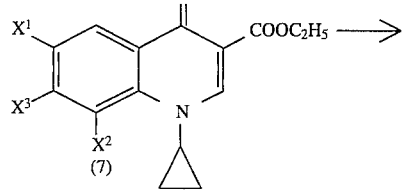

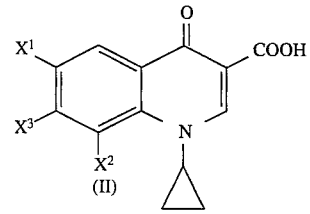

According to this, diethyl malonate (2) is acylated with the appropriate benzoyl fluoride or chloride (1), in the presence of magnesium ethylate, to give the aroylmalonic ester (3) (Organicum, 3rd edition, 1964, page 438).

By partial hydrolysis and decarboxylation of (3) in aqueous medium using catalytic amounts of sulphuric acid or p-toluenesulphonic acid, the ethyl. aroylacetates (4) are obtained in good yield, and these are converted with triethyl orthoformate/acetic anhydride into ethyl 2-(2,3,4,5-tetrahalogenobenzoyl)-3-ethoxyacrylates (5). The reaction of (5) with cyclopropylamine in a solvent such as, for example, methylene chloride, alcohol, chloroform, cyclohexane or toluene leads, in a slightly exothermic reaction, to the desired intermediate (6).

The cyclization reaction (6)→(7) is carried out in a temperature range of about 60° to 300° C., preferably 80° to 180° C.

The diluents which can be used are dioxane, dimethyl sulphoxide, N-methylpyrrolidone, sulpholane, hexamethylphosphoric trisamide and, preferably, N,N-dimethylformamide.

Suitable acid-binding agents for this reaction step are potassium tert.-butanolate, butyllithium, lithiumphenyl, phenyl magnesium bromide, sodium methylate, sodium hydride, sodium or potassium carbonate and, particularly preferably, potassium or sodium fluoride. It can be advantageous to use an excess of 10 mol-% of base.

The ester hydrolysis of (7) carried out in the last step under basic or acid conditions leads to the 1-cyclopropyl-6,7,8-trihalogeno-1,4-dihydro-4-oxo-3-quinolinecarboxylic acids (II).

The benzoyl halides (1) used as starting materials for this synthetic route are prepared as follows: 3,5-dichloro-2,4- difluorobenzoyl fluoride (boiling point 97°/20 mbar; $n_D^{20}$=1.5148) and 5-chloro-2,3,4-trifluoro-benzoyl fluoride (boiling point 68°-70°/20 mbar; $n_{DD}^{20}$=1.4764) are obtained together by heating tetrachlorobenzoyl chloride with potassium fluoride in sulpholane at elevated temperatures:

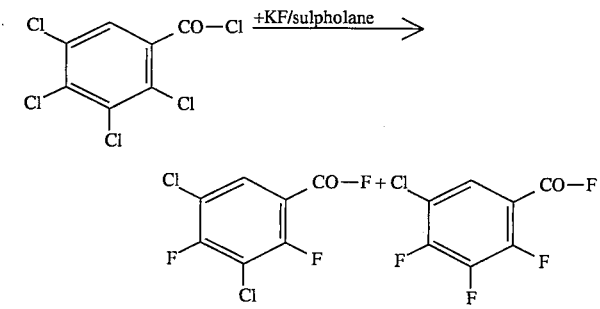

The chlorination of 2,4,5-trifluorobenzoic acid in chlorosulphonic acid leads to 3-chloro-2,4,5-trifluorobenzoic acid which is reacted as the crude product with thionyl chloride to give 3-chloro-2,4,5-trifluorobenzoyl chloride (boiling point 94°/18 mbar; $n_D^{20}$=1.5164):

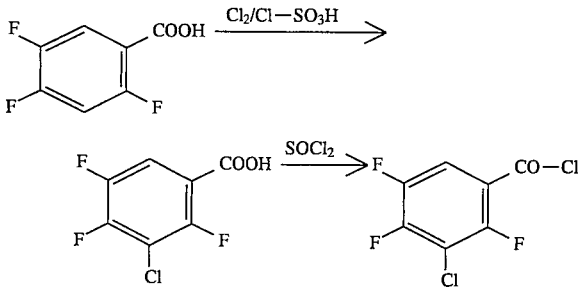

The amines (III) used as starting materials are known or can be obtained by processes known from the literature [U.S. Pat. No. 4,166,180, J. Med. Chem. 26, 1116 (1983). From the 2-arylpiperazines, the corresponding 2-cyclohexylpiperazines are obtained by catalytic hydrogenation; for example: 2-cyclohexylpiperazines (waxlike, melting point 71°-73° C.). Examples which may be mentioned are: morpholine, piperidine, thiomorpholine, pyrrolidine, piperazine, N-methylpiperazine, N-ethylpiperazine, N-(2-hydroxyethyl)piperazine, N-formylpiperazine, 2-methylpiperazine, 1,2-dimethylpiperazine, cis- and trans-2,5-dimethylpiperazine, cis- and trans-2,6-dimethylpiperazine, 2-ethylpiperazine, 2-propylpiperazine, 2-isopropylpiperazine, 2-isobutylpiperazine, 2-piperazinone, 1-methyl-2-piperazinone, 1-ethyl-2-piperazinone, 2-cyclohexyl-piperazine, 2-phenylpiperazine, 2-(4-chlorophenyl)piperazine, 2-(4-fluorophenyl)piperazine, 2-(4-bromophenyl)piperazine, 2-(4-methylphenyl)-piperazine, 2-(4-biphenylyl)-piperazine. 2-(4-methoxyphenyl)piperazine, 2(4-benzyloxyphenyl)piperazine, 2-(4-hydroxyphenyl)-piperazine, 2-(4-nitrophenyl)piperazine, 2-(3-nitrophenyl)piperazine, 2-(4-piperidinophenyl)piperazine, 2-(3,4-dimethoxyphenyl)piperazine, 2(3,4,5-trimethoxyphenyl)piperazine, 2-(3,4-dimethoxy-6methyl)piperazine, 2-(2-thienyl)piperazine and 3-aminopyrrolidine.

The compounds of the formula (V) which are used as starting materials are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-hexyl bromide formic acetic anhydride, acetic anhydride, propionic anhydride, acetyl chloride, chloroacetyl chloride, onic anhydride, acetyl chloride, chloroacetyl chloride, dichloroacetyl chloride, bromoacetyl bromide, butyryl chloride, 4-chlorobutyryl chloride, isobutyryl chloride, 4nitrophenyl ester of N-(tert.-butoxycarbonyl)-glycine, 4-nitrophenyl ester of N-(tert.-butoxycarbonyl)-L-alanine, 4-nitrophenyl ester of N-(tert.-butoxycarbonyl)-L-leucine, 4-nitrophenyl ester of N-(tert.-butoxycarbonyl)-L-valine, 3-methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamoyl chloride, methanesulphonyl chloride, ethanesulphonyl chloride, propane-1-sulphonyl chloride and formic acid.

The compounds of the formula (VII) which can be used according to the invention are known. Examples which may be mentioned are: acrylonitrile, methyl vinyl ketone, methyl acrylate and ethyl acrylate.

The reaction of (II) with (III) by method A is preferably carried out in a diluent such as dimethyl sulphoxide, N,N-dimethylformamide, hexamethylphosphoric trisamide, sulpholane, water, an alcohol, such as methanol, ethanol, n-propanol, isopropanol or glycol monomethyl ether, or pyridine. It is equally possible to use mixtures of these solvents, All customary inorganic and organic acid-binding agents can be used as the acid-binding agent. These preferably include the alkali metal hydroxides, alkali metal carbonates, organic amides and amidines. The following may be specifically mentioned as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. In general, the process is carried out between about 20° and 200° C., preferably between 80° and 180° C.

The reaction can be carried out under atmospheric pressure as w ell as under elevated pressure. In general, it is carried out under pressures between about 1 and about 100 bar , preferably between 1 and 10 bar.

When carrying out the process according to the invention, 1 to 15 moles, preferably 1 to 6 moles, of the amine (III) are used for 1 mole of carboxylic acid (II).

The reaction of (IV) with (V) is preferably carried out in a diluent such as dimethyl sulphoxide, dioxane, N,N-dimethylformamide, hexamethylphosphoric trisamide, sulpholane, water, an alcohol, such as methanol, ethanol, n-propanol, isopropanol or glycol monomethyl ether, or pyridine. It is equally possible to use mixtures of these diluents.

All customary inorganic and organic acid-binding agents can be used as the acid-binding agent. These preferably include the alkali metal hydroxides, alkali metal carbonates, organic amines and amidines. The following may be specifically mentioned as being particularly suitable: triethylamine, 1,4-diazabicyclo[2.2.2]octane (DABCO) or 1,8-diazabicyclo[5.4.0]undec-7-ene (DBU).

The reaction temperatures can be varied within a relatively wide range. In general, the process is carried out between about 20° and about 180° C., preferably between 0° and 110° C.

The reaction can be carried out under atmospheric pressure as well as under elevated pressure. In general, it is carried out under pressures between about 1 and about 100 bar, preferably between 1 and 10 bar.

When carrying out the process according to the invention by method B, 1 to 4 moles, preferably 1 to 1.5 mole, of the compound (V) is used for 1 mole of the compound (IV).

The reaction of (IV) with (VI) (method C) is preferably carried out in a diluent such as dioxane, dimethyl sulphoxide, N,N-dimethylformamide, methanol, ethanol, isopropanol, n-propanol or glycol monomethyl ether or in mixtures of these diluents.

The reaction temperatures can be varied within a relatively wide range. In general, the process is carried out between about 20° C. and about 150° C., preferably between 50° C. and 100° C.

The reaction can be carried out under atmospheric pressure as well as under elevated pressure. In general, it is carried out under pressures between about 1 and about 100 bar, preferably between 1 and 10 bar.

When carrying out the process according to the invention by method C, 1 to 5 moles, preferably 1 to 2 moles, of the compound (VI) are used for 1 mole of the compound (IV).

Apart from the compounds listed in the examples, the following may be specifically mentioned as new active compounds: 6-chloro-7-[3-(4-chlorophenyl)-1-piperazinyl]-1-cyclopropyl-8-fluoro-1,4-dihydro-4-oxo-3-quinolinecarboxylic acid, 6-chloro-1-cyclopropyl-8-fluoro-7-[3-(4-fluorophenyl)-1-piperazinyl]-1,4-dihydro-4-oxo-3-quinolinecarboxylic acid, 7-[3-(4-bromophenyl)-1-piperazinyl]-6-chloro-1-cyclopropyl-8-fluoro-1,4-dihydro-4-oxo-3-quinolinecarboxylic acid, 6-chloro-1-cyclopropyl-8-fluoro-1,4-dihydro-7-[3-(4-methylphenyl)-1-piperazinyl]-4-oxo-3-quinolinecarboxylic acid, 7-[3-(4-biphenyl) -1-piperazinyl]-6-chloro-1-cyclopropyl-8-fluoro-1,4-dihydro-4-oxo-3-quinolinecarboxylic acid, 6-chloro-1-cyclopropyl-8-fluoro-1,4-dihydro-7-[3-(4-methoxyphenyl)-1-piperazinyl]-4-oxo-3-quinolinecarboxylic acid, 6-chloro-1-cyclopropyl-8-fluoro-1,4-dihydro-7-[3-(4-hydroxyphenyl) -1-piperazinyl]-4-oxo-3-quinolinecarboxylic acid, 8-chloro-1-cyclopropyl-6-fluoro-1,4-dihydro-4-oxo-7-(3-phenyl-1-piperazinyl)-3-quinolinecarboxylic acid, 8-chloro-1-cyclopropyl-6-fluoro-1,4-dihydro-4-oxo-7-[(4-nitrophenyl)-1-piperazinyl]-3-quinolinecarboxylic acid, 8-chloro-1-cyclopropyl-6-fluoro-1,4-dihydro-4-oxo-7-[3-(4-piperidino-phenyl)-1-piperazinyl]-3-quinolinecarboxylic acid, 8-chloro-1-cyclopropyl-6-fluoro-1,4-dihydro-4-oxo-7-[3-(3,4-dimethoxy-phenyl)-1-piperazinyl]-3-quinolinecarboxylic acid, 8-chloro-1-cyclopropyl-6-fluoro-1,4-dihydro-4-oxo-7-[3-(3,4,5-trimethoxy-phenyl)-1-piperazinyl]-3-quinolinecarboxylic acid, 8-chloro-1-cyclopropyl-6-fluoro-1,4-dihydro-4-oxo-7-[3-(2-thienyl)-1-piperazinyl]-3-quinolinecarboxylic acid, 8-chloro-1-cyclopropyl-6-fluoro-1,4-dihydro-4-oxo-7-piperidino-3-quinolinecarboxylic acid, 7-(3-amino-1-pyrrolidinyl)-8-chloro-1-cyclopropyl-6-fluoro-1,4-dihydro-4-oxo-3-quinolinecarboxylic acid, 6,8-dichloro-1-cyclopropyl-1,4-dihydro-4-oxo-7-(1-piperazinyl)-3-quinolinecarboxylic acid, 7-(4-acetyl-1-piperazinyl)-6,8-dichloro-1-cyclopropyl-1,4-dihydro-4-oxo-3-quinolinecarboxylic acid, 7-(4-acetyl-1-piperazinyl)-6-chloro-1-cyclopropyl-8-fluoro-1,4-dihydro-4-oxo-3-quinolinecarboxylic acid, 6-chloro-1-cyclopropyl-8-fluoro-1,4-dihydro-7-(4-isopropyl-1-piperazinyl)-4-oxo-3-quinolinecarboxylic acid, 6-chloro-1-cyclopropyl-8-fluoro-1,4-dihydro-4-oxo-7-morpholino-3-quinolinecarboxylic acid, 6-chloro-1-cyclopropyl-8-fluoro-1,4-dihydro-4-oxo-7-thiomorpholino-3-quinolinecarboxylic acid and 8-chloro-1-cyclopropyl-7-(4-ethyl-3-oxo-1-piperazinyl)-6-fluoro-1,4-dihydro-4-oxo-3-quinolinecarboxylic acid.

The examples which follow illustrate the invention:

EXAMPLE A

6-Chloro-1-cyclopropyl-7,8-difluoro-1,4-dihydro-4-oxo-3-quinolinecarboxylic acid

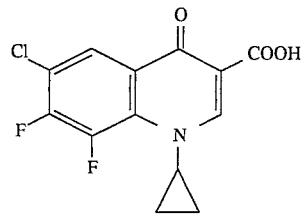

15.7 g (0.65 mole) of magnesium turnings are stirred in 40 ml of ethanol and 2 ml of tetrachloromethane and, after the reaction has started, 103 g (0.64 mole) of diethyl malonate in 80 ml of ethanol and 250 ml of toluene are added dropwise at 50°–60°. The mixture is stirred at this temperature for 1 hour, cooled to −5° to −10°, a solution of 138 g (0.65 mole) of 5-chloro-2,3,4-benzoyl fluoride in 63 ml of toluene is added dropwise, and the mixture is stirred further at 0° for 1 hour and allowed to stand overnight at room temperature. It is then heated at 40°–50° for 2 hours, cooled, and 250 ml of ice-water and 38.5 ml of concentrated sulphuric acid are added. The organic phase is separated off, the aqueous phase is extracted with 2 x 150 ml of toluene, and the combined organic phases are washed with saturated sodium chloride solution, dried with sodium sulphate and concentrated.

200 ml of water are added to the residue (it is advantageous to add 0.4 g of 4-toluenesulphonic acid at this point) and the mixture is heated under reflux for 5 hours for the deethoxycarbonylation. The mixture is extracted with 3 x 200 ml of dichloromethane, and the extracts are washed with saturated sodium chloride solution, dried with sodium sulphate, concentrated and distilled under high vacuum. 103 g (56.5%) of ethyl (5-chloro-2,3,4-trifluorobenzoyl)-acetate with a boiling point of 110°/0.9 Torr are obtained.

103 g (0.37 mole) of the ester obtained and 83 g (0.56 mole) of triethyl orthoformate are heated with 95 g of acetic anhydride at 150°–160° for 2 hours and then concentrated at 120°–130° under atmospheric pressure and thereafter under high vacuum. 115 g (92% of theory) of ethyl 2-(5-chloro-2,3,4-trifluorobenzoyl)-3-ethoxyacrylate are obtained as an oil.

14.8 g (0.26 mole) of cyclopropylamine are added dropwise to 84.1 g (0.25 mole) of this compound in 170 ml of ethanol, cooling in ice, and the mixture is stirred at room temperature for 2 hours. It is then stirred with 170 ml of water, cooled in ice, and the precipitate which has separated out is filtered off with suction, washed with water and a little methanol and dried. 47 g (54%) of ethyl 2-(5-chloro-2,3,4-trifluorobenzoyl)-3-cyclopropyl aminoacrylate of melting point 71–73° are obtained. The product is a cis/trans mixture according to the $^1$H NMR spectrum.

47 g (0.14 mole) of this compound in 230 ml of dimethylformamide are heated with 9.7 g (0.23 mole) of sodium fluoride at 160°–170° for 2 hours. The reaction mixture is poured into 400 ml of ice-water, and the precipitate is filtered off with suction, washed with water and dried. 44 g (99%) of ethyl 6-chloro-1-cyclopropyl-7,8-difluoro-1,4-dihydro-4-oxo-3-quinolinecarboxylate of melting point 169°–172° are isolated.

33 ml of concentrated sulphuric acid are added to 44 g (0.13 mole) of the quinolinecarboxylic ester in 300 ml of glacial acetic acid and 179 ml of water and the reaction mixture is heated at 150° C. for 2 hours. It is stirred into 400 ml of ice-water, and the precipitate is filtered off with suction, washed with water and dried. 37 g of theory) of 6-chloro-1-cyclopropyl-7,8-difluoro-1,4-dihydro-4-oxo-3-quinolinecarboxylic acid are isolated with melting point of 200°–204°.

EXAMPLE B

8-Chloro-1-cyclopropyl-6,7-difluoro-1,4-dihydro-4-oxo-3-quinolinecarboxylic acid

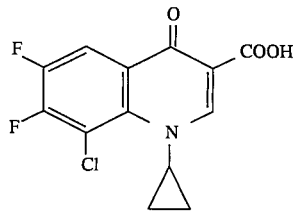

3-Chloro-2,4,5-trifluorobenzoyl chloride is reacted in analogy to Example A, the following steps being passed through: ethyl (3-chloro-2,4,5-trifluorobenzoyl)acetate as the enol (yield: 42%, melting point 72–75), ethyl 2-(3-chloro-2,4,5-trifluorobenzoyl)-3-ethoxyacrylate (crude yield: 95% oil), ethyl 2-(3-chloro-2,4,5-trifluorobenzoyl)3-cyclopropylaminoacrylate (yield: 67%, melting point 78°–80°), ethyl 8-chloro-1-cyclopropyl-6,7-difluoro-1,4-dihydro-4-oxo-3-quinolinecarboxylate (yield: 85%, melting point 154°–157°), 8-Chloro-1-cyclopropyl-6,7-difluoro-1,4-dihydro-4-oxo-3-quinolinecarboxylic acid (yield: 97.6%, melting point 189°–192°).

EXAMPLE C 6,8-Dichloro-1-cyclopropyl-7-fluoro-1,4-dihydro-4-oxo-3-quinolinecarboxylic acid

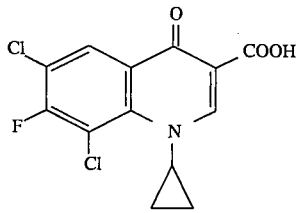

3,5-Dichloro-2,4-difluorobenzoyl fluoride is reacted in analogy to Example A, the following steps being passed through: ethyl (3,5-dichloro-2,4-difluorobenzoyl)acetate (yield: 43%, melting point 133°/2.5 Torr), ethyl 2-(3,5-dichloro-2,4-difluorobenzoyl)-3-ethoxyacrylate (crude yield: 95% oil), ethyl 2-(3,5-dichloro-2,4-difluorobenzoyl)-3-cyclopropylaminoacrylate (yield: 96%, melting point 71°–74°), ethyl 6,8-dichloro-1-cyclopropyl-7-fluoro-1,4-dihydro-4-oxo-3-quinolinecarboxylate (yield: 97%, melting point 215°–217° with decomposition), 6,8-dichloro-1-cyclopropyl-7-fluoro-1,4-dihydro-4-oxo-3-quinolinecarboxylic acid (yield: 93%, melting point 204°–206°).

EXAMPLE 1

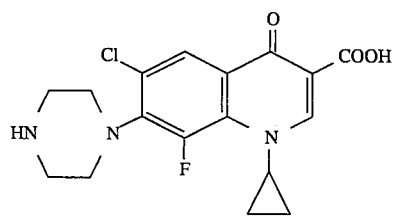

12 g (40 mmol) of the product from Example A in 100 ml of pyridine are heated with 17.2 g (0.2 mole) of piperazine under reflux for 5 hours. The mixture is concentrated in vacuo, the residue is stirred with 120 ml of water and the pH is adjusted to 5 with 2N hydrochloric acid. The precipitate is filtered off with suction, washed with water and methanol, boiled in 80 ml of methanol and dried. 12.3 g (84% of theory) 6-chloro-1-cyclopropyl-8-fluoro-1,4-dihydro-4-oxo-7-(1-piperazinyl)-3-quinolinecarboxylic acid of melting point 295°–298° (with decomposition) are obtained.

The following 6-chloro-1-cyclopropyl-8-fluoro-1,4-dihydro-4-oxo-3-quinolinecarboxylic acids substituted in the 7-position are obtained in analogy to Example 1:

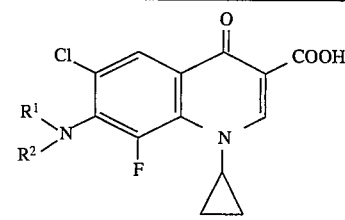

| Example | $\begin{array}{c}R^1\\R^2\end{array}\!\!N-$ | Melting point |
|---|---|---|
| 2 | ![HN-piperazine-CH3]  HN   N—, CH₃ | 258–282° (decomposition) |
| 3 | HN   N—, C₂H₅ | 191–195° (decomposition) |
| 4 | HN   N—, H₃C CH₃ | above ~274° (decomposition) |
| 5 | CH₃, HN   N—, CH₃ | 255–261° (decomposition) |

-continued

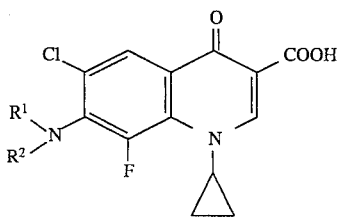

| Example | R¹\N—R²/ | Melting point |
|---|---|---|
| 6 | H₃C—N⌒N— ·HCl | >320° (decomposition) |
| 7 | HO—CH₂CH₂—N⌒N— | 276–280° (decomposition) |
| 8 | HN⌒N— with cyclohexyl | above ~190° (decomposition) |
| 9 | HN⌒N— with benzyl | 154–158 |

EXAMPLE 10

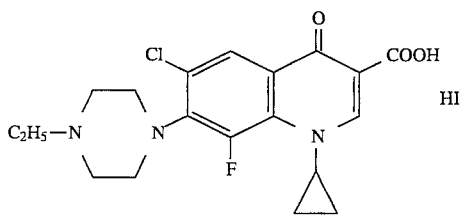

1.83 g (5 mmol) of the product from Example 1 in 20 ml of dimethylformamide are heated with 1.6 g of ethyl iodide and 1 g of triethylamine at 80° for 3 hours. The reaction mixture is concentrated in vacuo, and the residue is stirred with 20 ml of water and recrystallized from methanol. 0.4 g (15% of theory) of 6-chloro-1-cyclopropyl-7-(4-ethyl-1-piperazinyl)-8-fluoro-1,4-dihydro-4-oxo-3-quinolinecarboxylic acid of melting point 237°–242° (with decomposition) is obtained.

EXAMPLE 11

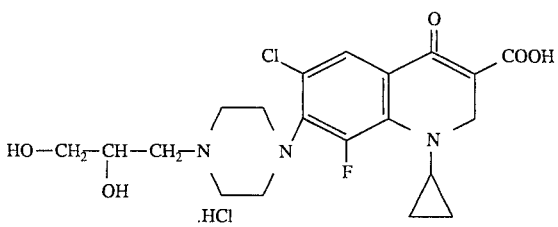

3.65 g (0.01 mmol) of the product from Example 1 are suspended in 150 ml of ethanol and 30 ml of water, the suspension is adjusted to pH 4.6 with acetic acid, and then, at room temperature, 3.4 g (0.02 mol) of 2,3-cyclohexylideneglyceraldehyde and, in portions, 950 mg of sodium cyanoborohydride are added. The mixture is stirred at room temperature overnight, the pH is adjusted to 8 with sodium bicarbonate, extraction with dichloromethane is carried out, and the extract is concentrated. 3 ml of concentrated hydrochloric acid are added to the residue in 25 ml of ethanol and 25 ml of water, and the mixture is heated under reflux for 6 hours. It is concentrated, the residue is dissolved in water, the solution is extracted with dichloromethane, concentration is again carried out, and the residue is stirred with ethanol and dried. 1.3 g of 6-chloro-1-cyclopropyl-8-fluoro-1,4-dihydro-7-[4-(2,3-dihydroxypropyl)-1-piperazinyl]-4-oxo-3-quinolinecarboxylic acid hydrochloride of melting point 263°–266° (with decomposition) is obtained.

EXAMPLE 12

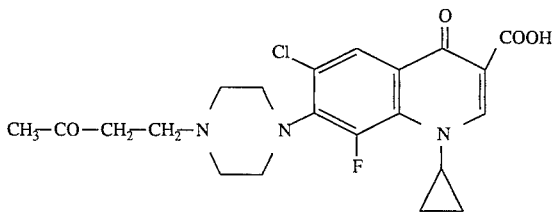

1.83 g (5 mmol) of the product from Example 1 and 1.95 g (28 mmol) of methyl vinyl ketone in 25 ml of ethanol are heated under reflux for 6 hours, and the precipitate is filtered off with suction and recrystallized from glycol monomethyl ether. 1 g (46% of theory) of 6-chloro-1-cyclopropyl-8-fluoro-1,4-dihydro-4-oxo-7-[4-(3 -oxobutyl) -1-piperazinyl] -3-quinolinecarboxylic acid of melting point 187°–190° (with decomposition) is obtained.

EXAMPLE 13

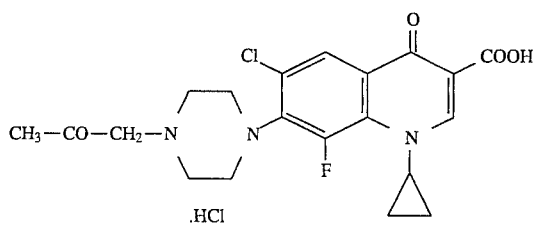

1.83 g (5 mmol) of the product from Example 1 in 25 ml of ethanol are heated with 1.95 g (20 mmol) of chloroacetone under reflux for 6 hours. The suspension is cooled, and the precipitate is filtered off with suction, thoroughly washed with ethanol and dried in vacuo, 1 g (44% of theory) of 6-chloro-1-cyclopropyl-8-fluoro-1,4-dihydro-4-oxo-7-[4-(2-oxopropyl)-1-piperazinyl]-3-quinolinecarboxylic acid hydrochloride of melting point ~ 320° C. (with decomposition) being obtained.

EXAMPLE 14

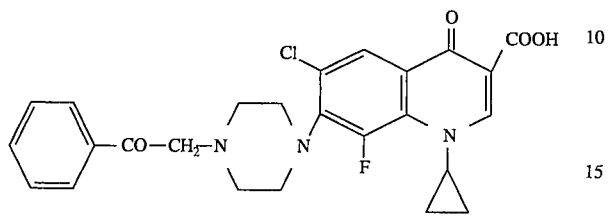

3.66 g (0.01 mole) of the product from Example 1 in 50 ml of dimethylformamide are heated with 2.2 g of ω-chloroacetophenone and 2.2 g of triethylamine at 60° for 10 hours. The reaction mixture is concentrated in vacuo, the residue is stirred with 30 ml of water, and the precipitate is filtered off with suction, washed with water and recrystallized from acetone. 1.2 g (25% of theory) of 6-chloro-1-cyclopropyl-8-fluoro-1,4-dihydro-4-oxo-7-[4-(2-oxo-2-phenylethyl)-1-piperazinyl]-3-quinolinecarboxylic acid of melting point 175°–179° (with decomposition) is obtained.

EXAMPLE 15

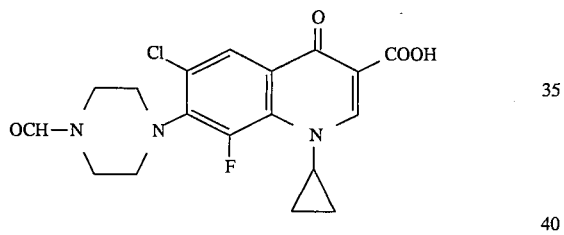

1.5 g (4 mmol) of the product from Example 1 are dissolved in a mixture of 10 ml of dioxane and 170 mg of sodium hydroxide in 2.5 ml of water and then, simultaneously, a solution of 0.7 g of formic acetic anhydride in 5 ml of dioxane and a solution of 340 mg of sodium hydroxide in 5 ml of water are added. The mixture is stirred at room temperature for 2 hours, diluted with 30 ml of water, and the precipitate is filtered off with suction, washed with water and methanol and recrystallized from glycol monomethyl ether. 0.6 g (38%) of 6-chloro-1-cyclopropyl-8-fluoro-7-(4-formyl-1-piperazinyl)-1,4-dihydro-4-oxo-3-quinolinecarboxylic acid of melting point 277°–278° (with decomposition) is obtained.

EXAMPLE 16

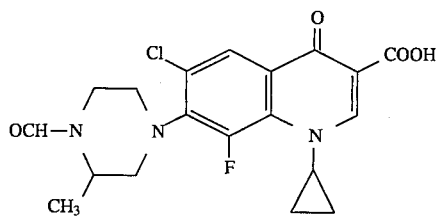

When the product from Example 2 is reacted in analogy to Example 15, then 6-chloro-1-cyclopropyl-8-fluoro-7-(4-formyl-3-methyl-1-piperazinyl)-1,4-dihydro-4-oxo-3-quinolinecarboxylic acid of melting point 280°–282° (with decomposition) is obtained.

EXAMPLE 17

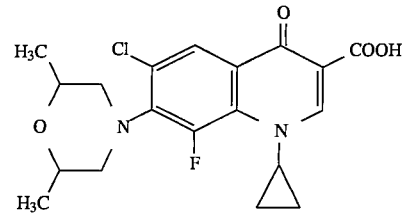

3 g (10 mmol) of the product from Example A in 35 ml of dimethyl sulphoxide are heated at 140° with 1.2 g (10 mmol) of 2,6-dimethylmorpholine and 2.2 g (20 mmol) of diazabicyclo[2.2.2]octane for 5 hours. The mixture is concentrated under high vacuum, stirred with 30 ml of water, the pH is adjusted to 6 with 2N hydrochloric acid, and the precipitate is filtered off with suction and recrystallized from glycol monomethyl ether. 1.6 g (41% of theory) of 6-chloro-1-cyclopropyl-8-fluoro-1,4-dihydro-7-(2,6-dimethyl-4-morpholinyl)-4-oxo-3-quinolinecarboxylic acid of melting point 258°–261° (with decomposition) is obtained.

EXAMPLE 18

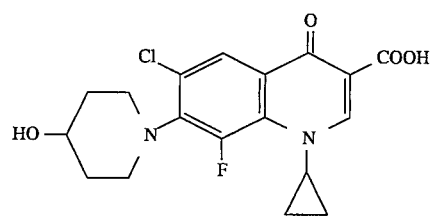

When the product from Example A is reacted with 4-hydroxypiperidine in analogy to Example 17, then 6-chloro-1-cyclopropyl-8-fluoro-1,4-dihydro-7-(4-hydroxy-1-piperidinyl)-4-oxo-3-quinolinecarboxylic acid of melting point 226°–231° (with decomposition) is obtained.

EXAMPLE 19

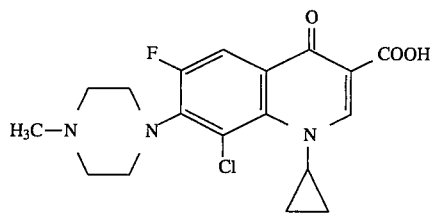

3 g (0.01 mole) of the product from Example B in 25 ml of pyridine are heated with 4 g (0.04 mole) of 1-methylpiperazine under reflux for 5 hours. The mixture is concentrated in vacuo, 20 ml of water are added, the pH is adjusted to 5 with 2N hydrochloric acid, and the precipitate which has separated out is recrystallized from methanol. 0.6 g (16% of theory) of 8-chloro-1-cyclopropyl-6-fluoro-1,4-dihydro-7-(4-methyl-1-piperazinyl)-4-oxo-3-quinolinecarboxylic acid of melting point 293°–297° (with decomposition) is obtained.

EXAMPLE 20

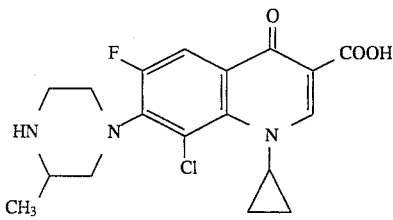

In analogy to Example 19, with 2-methylpiperazine, 8-chloro-1-cyclopropyl-6-fluoro-1,4-dihydro-7-(3-methyl-piperazinyl)-4-oxo-3-quinolinecarboxylic acid of melting point 318°–325° (with decomposition) is obtained.

EXAMPLE 21

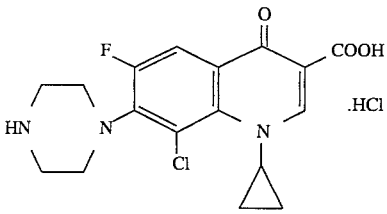

In analogy to Example 19, the product from Example B is reacted with piperazine under reflux for 1.5 hours, and the reaction mixture is treated with hydrochloric acid, 8-chloro-1-cyclopropyl-6-fluoro-1,4-dihydro-7-(1-piperazinyl)-3-quinolinecarboxylic acid hydrochloride with a decomposition point above 330° being obtained.

EXAMPLE 22

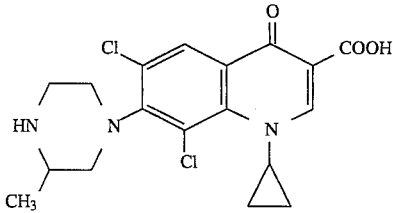

When the product from Example C is reacted with 2-methylpiperazine in analogy to Example 19, then 6,8-dichloro-1-cyclopropyl-1,4-dihydro-7-(3-methyl-1-piperazinyl)-4-oxo-3-quinolinecarboxylic acid of melting point 288°–291° (with decomposition) is obtained.

EXAMPLE 23

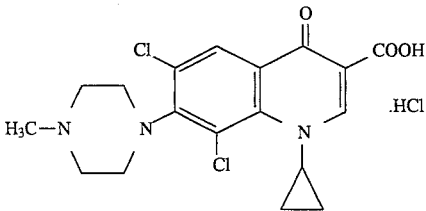

3.2 g (0.01 mole) of the product from Example C are heated with 4 g (0.04 mole) of 1-methylpiperazine at 80° for 3 days, the reaction mixture is concentrated in vacuo, and the residue is taken up in a little water and the pH is adjusted to 7 with 2N hydrochloric acid. Crystallization takes place on standing in ice. The precipitate was filtered off with suction and recrystallized from water with the addition of a little hydrochloric acid. 0.6g 6,8-dichloro-1-cyclopropyl-1,4-dihydro-7-(4-methyl-1-piperazinyl)-4-oxo-3-quinolinecarboxylic acid of melting point >300° is obtained.

EXAMPLE 24

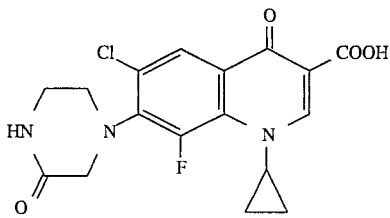

3 g (10 mmol) of the product from Example 1 in 25 ml of dimethyl sulphoxide are heated with 1.8 g (18 mmol) of 2-piperazinone and 2.2 g (20 mmol) of diazabicyclo-[2.2.2] octane at 130° for 2 hours. The suspension is adjusted to pH 5 with 2N hydrochloric acid, 25 ml of water are added, and the precipitate is filtered off with suction, extracted by boiling with 20 ml of methanol and dried. 1.5 g (39% of theory) of 6-chloro-1-cyclopropyl-8-fluoro-1,4-dihydro-4-oxo-7-(3-oxo-1-piperazinyl)-3-quinolinecarboxylic acid of melting point 288°–291° (with decomposition) is obtained.

| Example of a tablet according to the invention | |
| --- | --- |
| Each tablet contains: | |
| Compound of Example 1 | 583.0 mg |
| Microcrystalline cellulose | 55.0 mg |
| Corn starch | 72.0 mg |
| Poly(1-vinyl-2-pyrrolidone) insoluble | 30.0 mg |
| Highly disperse silica | 5.0 mg |
| Magnesium stearate | 5.0 mg |
| | 750.0 mg |
| The lacquer coating contains: | |
| Poly(O-hydroxypropyl O-methyl)-cellulose 15 cp | 6.0 mg |
| Macrogol 4000 rec. INN (polyethylene glycol DAB) | 2.0 mg |
| Titanium(IV) oxide | 2.0 mg |
| | 10.0 mg |

The compounds according to the invention have very low toxicity and exhibit a broad antibacterial spectrum towards Gram-positive and Gram-negative organisms, especially towards enterobacteriaceae; especially including those which are resistant to various antibiotics, such as, for example, penicillins, cephalosporins, aminoglycosides, sulphonamides and tetracylines.

These valuable properties make it possible to use them as chemotherapeutic active compounds in medicine and as substances to preserve inorganic and organic materials, especially organic materials of all types, for example polymers, lubricants, dyes, fibers leather, paper and wood, and foodstuffs and water.

The compounds according to the invention are active against a very broad spectrum of microorganisms. Using them, it is possible to control Gram-negative and Gram-positive bacteria and bacteroid microorganisms and to prevent, ameliorate and/or heal illnesses caused by these pathogens.

The compounds according to the invention are particularly active against bacteria and bacteroid microorganisms. Thus, they are especially suitable for the prophylaxis and chemotherapy of local and systemic infections caused by these pathogens in human and veterinary medicine.

For example, local and/or systemic illnesses which are caused by the following pathogens or by mixtures of the following pathogens can be treated and/or prevented: micrococcaceae, such as Staphylococci, for example *Staphylococcus aureus, Staph. epidermidis*, (Staph.=Staphylococcus); Lactobacteriaceae, such as Streptococci, for example *Streptococcus pyogenes*,α- and β-haemolytic Streptococci, non-γ-haemolytic Streptococci, Enterococci and *Diplococcus pneumoniae* (Pneumococci) (Str.=Streptococcus); Enterobacteriaceae, such as Escherichiae bacteria of the Escherichia group, for example *Escherichia coli*, Enteobacte bacteria, for example *E. aeogenes* and *E. cloacae* (E.=Enterobacter), Klebsiella bacteria, for example *K. pneumoniae* (K.=Klebsiella), Serratia, for example *Serratia marcescens*, Proteae bacteria of the Proteus group: Proteus, for example *Pr. vulgaris, Pr. morganii, Pr. rettgeri* and *Pr. mirabilis* (Pr.=Proteus); Pseudomonadaceae, such as Pseudomonas bacteria, for example *Ps. aeruginosa* (Ps.=Pseudomonas); Bacteroidaceae, such as Bacteroides bacteria, for example *Bacteroides fragilis* Mycoplasma, for example *Mycoplasma pneumoniae*, also Mycobacteria, for example *Mycobacterium tuberculosis, Mycobacterium leprae* and atypical Mycobacteria.

The above list of pathogens is purely illustrative and is in no way to be interpreted as restrictive. The following may be mentioned as examples of illnesses which can be prevented, ameliorated and/or healed by the compounds according to the invention: otitis; pharyngitis; pneumonia; peritonitis; pyelonephritis; cystiris; endocarditis; systemic infections; bronchitis; arthritis; local infections and septic illnesses.

The present invention includes pharmaceutical preparations which in addition to non-toxic, inert pharmaceutically vehicles contain one or more compounds according to the invention or which consist of one or more active compounds according to the invention, and processes for the production of these preparations.

The present invention also includes pharmaceutical preparations in dosage units. This means that the preparation are in the form of individual parts, for example tablets, coated tablets, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary vehicles such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium and magnesium stearate and solid polyethylene glycols, or mixtures of these substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acids), or mixtures of these substances.

Ointments, pastes, creams and gels can contain the customary vehicles in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary vehicles in addition to the active compound or compounds, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary vehicles in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol,1,3-butylene glycol, dimethylformamide, oils, especially cottonseed oil, groundnut oil, maize germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain colourants, preservatives and additives which improve the odor and flavor, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutically active compounds in addition to the compounds according to the invention.

The abovementioned pharmaceutical preparations are manufactured in the usual manner according to known methods, for example by mixing the active compound or compounds with the vehicle or vehicles.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds in amounts of about 0.5 to about 500, preferably 5 to 100, mg/kg of body weight every 24 hours, optionally in the form of several individual administrations, in order to achieve the desired results. An individual administration contains the active compound or compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place.

Thus, it can suffice in some cases to manage with less than the above mentioned amount of active compound, whilst in other cases the abovementioned amount of active compound must be exceeded. The particular required optimum dosage and the type of administration of the active compounds can easily be decided by anyone skilled in the art, on the basis of his expert knowledge.

The new compounds can be administered in the customary concentrations and preparations together with the feed or with the feed preparations or with the drinking water. By this means, it is possible to prevent, ameliorate and/ or heal an infection by Gram-negative or Gram-positive bacteria and by this means to achieve a promotion of growth and an improvement in the utilization of the feed.

The MIC values of some of the compounds according to the invention are indicated in the table below.

As a comparison, corresponding MIC values for 1-ethyl-6-fluoro-1,4-dihydro-4-oxo-7-(1-piperazinyl)-3-quinolinecarboxylic acid ("norfloxacin"), which is disclosed in J. Med. Chem. 23, 1358 (1980), have been indicated, it emerging that the compounds according to the invention are superior to the known compounds.

| strain | | \multicolumn{11}{c}{MIC (mcg/ml) Example No.} | | | | | | | | | | |
|---|---|---|---|---|---|---|---|---|---|---|---|---|
| | | 1 | 2 | 3 | 5 | 6 | 7 | 8 | 10 | 17 | 12 | 13 |
| E. coli | Neuman | ≦0.015 | ≦0.015 | ≦0.015 | ≦0.015 | ≦0.015 | ≦0.015 | ./. | ≦0.015 | ./. | ≦0.015 | ≦0.015 |
| | T 7 | ≦0.015 | ≦0.015 | ≦0.015 | ≦0.015 | ≦0.015 | ≦0.015 | ≦0.015 | 0.025 | ./. | ≦0.015 | ≦0.015 |
| | 445/7 | 4 | 8 | 8 | 8 | 4 | 16 | ./. | 16 | ./. | 8 | 8 |
| Klebsiella | 63 | ≦0.015 | 0.03 | 0.03 | 0.03 | 0.015 | 0.06 | ./. | 0.125 | ./. | ≦0.015 | ≦0.015 |
| | 6179 | 0.03 | 0.03 | ≦0.015 | 0.03 | 0.015 | 0.06 | ./. | 0.06 | ./. | 0.06 | 0.06 |
| Proteus | 1017 | ≦0.015 | ./. | ./. | ./. | 0.06 | 0.125 | ./. | ./. | ./. | 0.03 | ≦0.015 |
| Providencia | 12012 | ≦0.015 | 0.03 | ./. | ./. | 0.03 | ./. | ./. | ./. | ./. | ≦0.015 | ≦0.015 |
| | 12052 | 8 | 16 | 16 | 32 | 4 | 16 | ./. | ./. | ./. | 16 | 16 |
| Staph. FK | 422 | 0.25 | 0.25 | 0.25 | 0.25 | 0.025 | 0.5 | 0.06 | ./. | ≦0.015 | 0.25 | 0.25 |
| | 1756 | 0.25 | 0.5 | 0.25 | 0.5 | 0.5 | 0.5 | 0.06 | ./. | ≦0.015 | 0.25 | 0.25 |
| | 133 | 0.25 | 0.25 | 0.25 | 0.5 | 0.25 | 0.25 | 0.06 | ./. | ./. | 0.25 | 0.25 |
| Pseudom. | Ellsworth | 0.06 | ./. | ./. | ./. | ./. | ./. | ./. | ./. | ./. | 0.125 | 0.125 |

| | | | Example No. | | | | | |
|---|---|---|---|---|---|---|---|---|
| | Strain | | 14 | 17 | 19 | 20 | 21 | 22 | Norfloxacin |
| E.coli | Neumann | | ≦0.015 | ./. | ≦0.015 | ≦0.015 | ≦0.015 | ≦0.015 | 0.06 |
| | T 7 | | ≦0.015 | ./. | ≦0.015 | ≦0.015 | ≦0.015 | ≦0.015 | 0.03 |
| | 455/7 | | 2 | ./. | 1 | 1 | 1 | 2 | 16 |
| Klebsiella | 63 | | 0.06 | ./. | 0.03 | ≦0.015 | 0.06 | 0.03 | 0.125 |
| | 6179 | | 0.25 | ./. | 0.03 | 0.03 | 0.03 | 0.06 | 0.25 |
| Proteus | 1017 | | 0.125 | ./. | 0.03 | ≦0.015 | 0.03 | 0.06 | 0.03 |
| Providencia | 12012 | | 0.06 | ./. | 0.03 | 0.03 | 0.06 | 0.06 | 0.03 |
| | 12052 | | 16 | ./. | 4 | 4 | 1 | 2 | 64 |
| Staph. FK | 422 | | ./. | ≦0.015 | 0.06 | 0.06 | 0.125 | 0.125 | 0.5 |
| | 1756 | | ./. | ≦0.015 | 0.06 | 0.06 | 0.125 | 0.125 | 1 |
| | 133 | | ./. | ./. | 0.06 | 0.06 | 0.06 | 0.125 | 0.5 |
| Pseud. | Ellsworth | | ./. | ./. | 0.125 | 0.25 | ./. | ./. | 0.125 |

Agar dilution test/isosensitest medium

It will be understood that the specification and examples are illustrative but not limitative of the present invention and that other embodiments within the spirit and scope of the invention will suggest themselves to those skilled in the art.

What is claimed is:

1. A 7-amino-8-chloro-1-cyclopropyl-6-fluoro-1,4-dihydro-4-oxo-3-quinolinecarboxylic acid of the formula

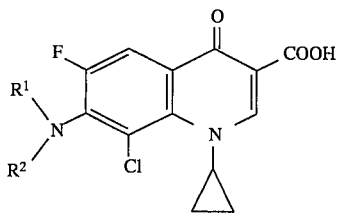

in which

R[1] and R[2], together with the nitrogen atom to which they are bonded, form a 5- or 6-membered heterocyclic ring which can contain in addition, as ring member, the group N—R[3] and which can optionally be substituted on the carbon atoms once or twice by $C_1$-$C_2$-alkyl, 2-thienyl, hydroxy, methoxy, amino, methylamino or ethylamino or phenyl which is optionally substituted once or twice by chlorine, fluorine, bromine, methyl, phenyl, hydroxyl, methoxy, benzyloxy, nitro or piperidino, R[3] represents hydrogen, a branched or unbranched alkyl having 1 to 4 carbon atoms which can optionally be substituted by hydroxyl or the alkoxycarbonyl group having 1 to 4 carbon atoms in the alcohol moiety, a phenacyl radical or an oxoalkyl radical having up to 4 carbon atoms or furthermore denotes the group —CHO or a pharmaceutically acceptable hydrate or acid addition, alkali metal, alkaline earth metal or guanidinium salt thereof.

2. A compound, hydrate or salt according to claim 1, in which

R[1] and R[2], together with the nitrogen atom to which they are bonded, can form a 5- or 6-membered heterocyclic ring which can have in addition, as ring member, the group N—R[3] and which can optionally be substituted on the carbon atoms once or twice by methyl, amino, methylamino, ethylamino or hydroxy and R[3] represents hydrogen, methyl or ethyl.

3. A compound, hydrate or salt according to claim 1, in which

R[1] and R[2] together with the nitrogen atom to which they are bonded, can form a 5- or 6-membered heterocyclic ring which can have in addition, as ring member, the groups N—R[3] and which can optionally be substituted on the carbon atoms once or twice by methyl or amino, and R[3] represents hydrogen or methyl.

4. A compound according to claim 1, wherein such compound is 8-chloro-1-cyclopropyl-6-fluoro-1,4-dihydro-7-(4-methyl-1-piperazinyl)-4-oxo-3-quinolinecarboxylic acid of the formula

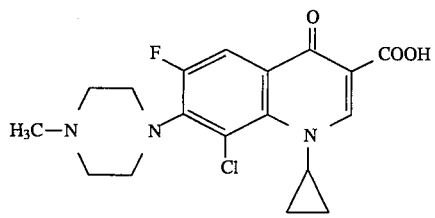

or a pharmaceutically acceptable hydrate or acid addition, alkali metal, alkaline earth metal or guanidine salt thereof.

5. A compound according to claim 22, wherein such compound is 8-chloro-1-cyclopropyl-6-fluoro-1,4-dihydro-7-(3-methyl-1-piperazinyl)-4-oxo-3-quinolinecarboxylic acid of the formula

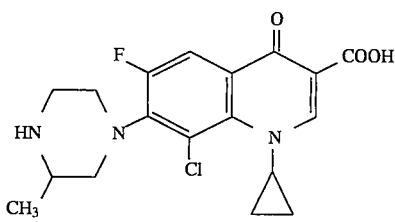

or a pharmaceutically acceptable hydrate or acid addition, alkali metal, alkaline earth metal or guanidine salt thereof.

6. A compound according to claim 1, wherein such compound is 8-chloro-1-cyclopropyl-fluoro-1,4-dihydro-4-oxo-7-(1-piperazinyl)-3-quinolinecarboxylic acid of the formula

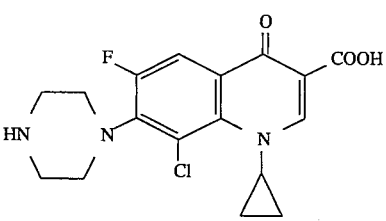

or a pharmaceutically acceptable hydrate or acid addition, alkali metal, alkaline earth metal or guanidine salt thereof.

7. An antibacterial composition comprising a diluent and an antibacterially effective amount of a compound, hydrate or salt according to claim 1.

8. A therapeutic method for chemotherapy of local or systemic infections caused by Gram-negative and Gram-positive bacteria or bacteroid microorganisms in an individual for whom such therapy is indicated, comprising administering to the individual an effective bactericidal amount of a 7-amino-1-cyclopropyl-8-chloro-6-fluoro-1,4-dihydro-4-oxo-3-quinoline-carboxylic acid or a hydrate or salt thereof according to claim 1.

\* \* \* \* \*

UNITED STATES PATENT AND TRADEMARK OFFICE
CERTIFICATE OF CORRECTION

PATENT NO. : 5,571,812
DATED : November 5, 1996
INVENTOR(S) : Petersen, et al.

It is certified that error appears in the above-indentified patent and that said Letters Patent is hereby corrected as shown below:

Col. 24, line 13    Delete claim " 22 " and substitute
line 1              -- 1 --

Col. 24, line 29    After " cyclopropyl- " insert -- 6- --

Signed and Sealed this

Twenty-fourth Day of June, 1997

Attest:

BRUCE LEHMAN

Attesting Officer    Commissioner of Patents and Trademarks